US00PP36333P3

(12) United States Plant Patent
Leis

(10) Patent No.: US PP36,333 P3
(45) Date of Patent: Dec. 24, 2024

(54) STRAWBERRY PLANT NAMED 'CIVH413'

(50) Latin Name: ***Fragaria* x *ananassa* Duchesne ex Rozier**
Varietal Denomination: CIVH413

(71) Applicant: C.I.V.-CONSORZIO ITALIANO VIVAISTI-SOCIETÀ CONSORTILE A R.L., Comacchio FE (IT)

(72) Inventor: Michelangelo Leis, Ferrara FE (IT)

(73) Assignee: C.I.V.-CONSORZIO ITALIANO VIVAISTI-SOCIETÀ CONSORTILE A R.L., Comacchio (IT)

( * ) Notice: Subject to any disclaimer, the term of this patent is extended or adjusted under 35 U.S.C. 154(b) by 16 days.

(21) Appl. No.: 17/979,712

(22) Filed: Nov. 2, 2022

(65) Prior Publication Data

US 2023/0140847 P1 May 4, 2023

(30) Foreign Application Priority Data

Nov. 4, 2021 (QZ) ..... PBR 2021/2768

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

*Primary Examiner* — Kent L Bell
(74) *Attorney, Agent, or Firm* — Foley & Lardner LLP

(57) ABSTRACT

This invention relates to a new and distinct variety of strawberry plant named 'CIVH413'. The new June bearing strawberry variety named 'CIVH413' is primarily adapted to the climate and growing conditions of continental climate and is characterized by a rustic plant with upright habit and visible fruit easy to collect; the vigour is medium. The new strawberry has a high productivity, consistent during all the picking season; in particular is tolerant to the most common leaf and root diseases. The fruits have conical, attractive and very regular shape with orange-red colour; the size is big and consistent during all the time of picking. The firmness is high with a very good shelf life. The flavour is very good, balanced and aromatic.

4 Drawing Sheets

Figure 1:
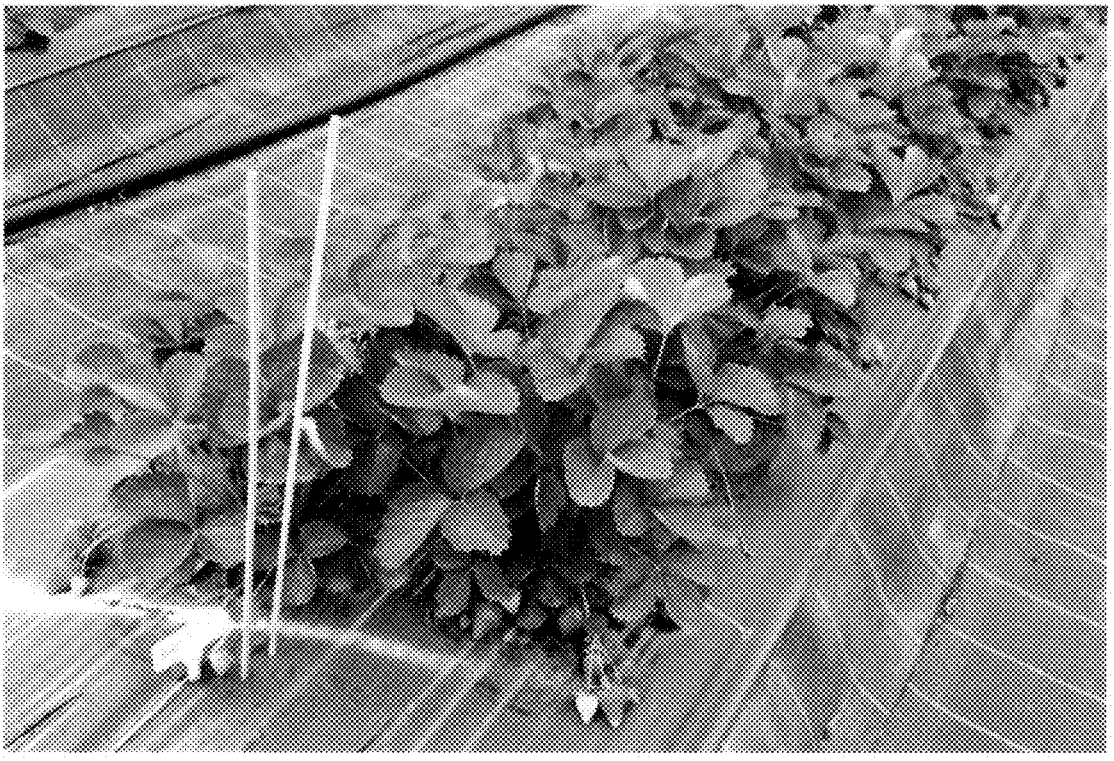

Latin name of the genus and species of the plant claimed: *Fragaria* x *ananassa* Duchesne ex Rozier.
Variety denomination: 'CIVH413'.

CROSS-REFERENCE TO RELATED APPLICATION

This application claims priority from Community Plant Variety Rights Application No. 2021/2768, filed Nov. 4, 2021.

BACKGROUND OF THE INVENTION

The present invention relates to a new and distinct strawberry variety named 'CIVH413'. The variety is botanically known as *Fragaria* x *ananassa* Duchesne ex Rozier.

The new strawberry 'CIVH413' is a product of a planned breeding program conducted by the inventor, Michelangelo Leis in San Giuseppe di Comacchio, Ferrara, Italy. The objective of the breeding program is to develop june bearing strawberry variety with high chill requirement, high and constant productivity during all the picking season; fruit with very regular and conical shape, easy to collect, big and constant fruit size, high firmness and very good shelf life. Rustic plant, tolerant to the most common leaf and root diseases.

This new strawberry 'CIVH413' is a result of a controlled cross made by the inventor in 2011, in San Giuseppe di Comacchio, Ferrara, Italy. The male or pollen parent is strawberry selection designated 6C9C-007 (unpatented proprietary selection). The female or seed parent is strawberry selection designated L7H3-017 (unpatented proprietary selection).

The new strawberry 'CIVH413' was discovered and selected by the inventor as a single flowering plant within the progeny of the stated cross in May 2013 in San Giuseppe di Comacchio, Ferrara, Italy (44°45' North and 12°11' East). After its selection, the new variety was asexually propagated by stolons in a nursery located in San Giuseppe di Comacchio, Ferrara, Italy. The new variety was extensively tested over the next several years in different European area with high chill condition. This propagation has demonstrated that the combination of characteristics as herein disclosed for the new cultivar are firmly fixed and retained through successive generations of asexual reproduction. The new cultivar reproduces true to type.

BRIEF SUMMARY OF THE INVENTION

'CIVH413' is primarily adapted to the climate and growing with high chill condition. This area provides the needed and correct temperatures for flower induction, and to produce a strong and vigorous plant, and to maintain fruit quality during full production.

The following traits have been repeatedly observed and are determined to be unique characteristics of 'CIVH413', which in combination distinguish this strawberry plant as a new and distinct variety:

1. Plants with upright habit, with cleary visible fruit.
2. Fruits are easy to collect.

3. Fruit with conical, attractive and very regular shape.
4. 'CIVH413' has high firmness and very good shelf life.
5. Post-harvest fruit longevity—6-8 days, if stored according to industry standards.
6. High productivity, consistent during all the picking season.
7. Tolerant to most common leaf and root diseases.

Plants of the new strawberry variety 'CIVH413' differ from plants of the parents, 6C9C-007 and L7H3-017 in the characteristics described in Table 1.

TABLE 1

| Characteristic | 'CIVH413' | 6C9C-007 | L7H3-017 |
|---|---|---|---|
| Time of ripening | Early | Medium | Early |
| Growth habit | Upright | Upright | Semi-upright |
| Plant vigour | Medium | Medium to strong | Strong |
| Fruit size | Large | Medium | Large to very large |
| Firmness | High | Medium to high | Medium |

Of the many commercial cultivars known to the present inventor, the most similar in comparison to the new strawberry variety 'CIVH413' is the strawberry variety 'CLERY' (unpatented). Plants of the new strawberry variety 'CIVH413' differ from plants of strawberry variety 'CLERY' (unpatented) in the characteristics described in Table 2:

TABLE 2

| Characteristic | 'CIVH413' | 'CLERY' (unpatented) |
|---|---|---|
| Fruit: time of beginning ripening | Early | Very early |
| Fruit: colour | Orange red | Medium red |
| Plant: growth habit | Upright | Semi-upright |

BRIEF DESCRIPTIONS OF THE PHOTOGRAPHS

The accompanying color photographs illustrate the overall appearance of typical specimens of the new strawberry variety 'CIVH413', at various stages of development as true as it is reasonably possible with color reproductions of this type. Color in the photographs may differ slightly from the color value cited in the botanical description which accurately describe the color of 'CIVH413'. The depicted plant and plant parts of the new strawberry variety 'CIVH413' were taken in San Giuseppe di Comacchio, Ferrara, Italy, and are approximately 6 to 9 months old.

Figure 2:
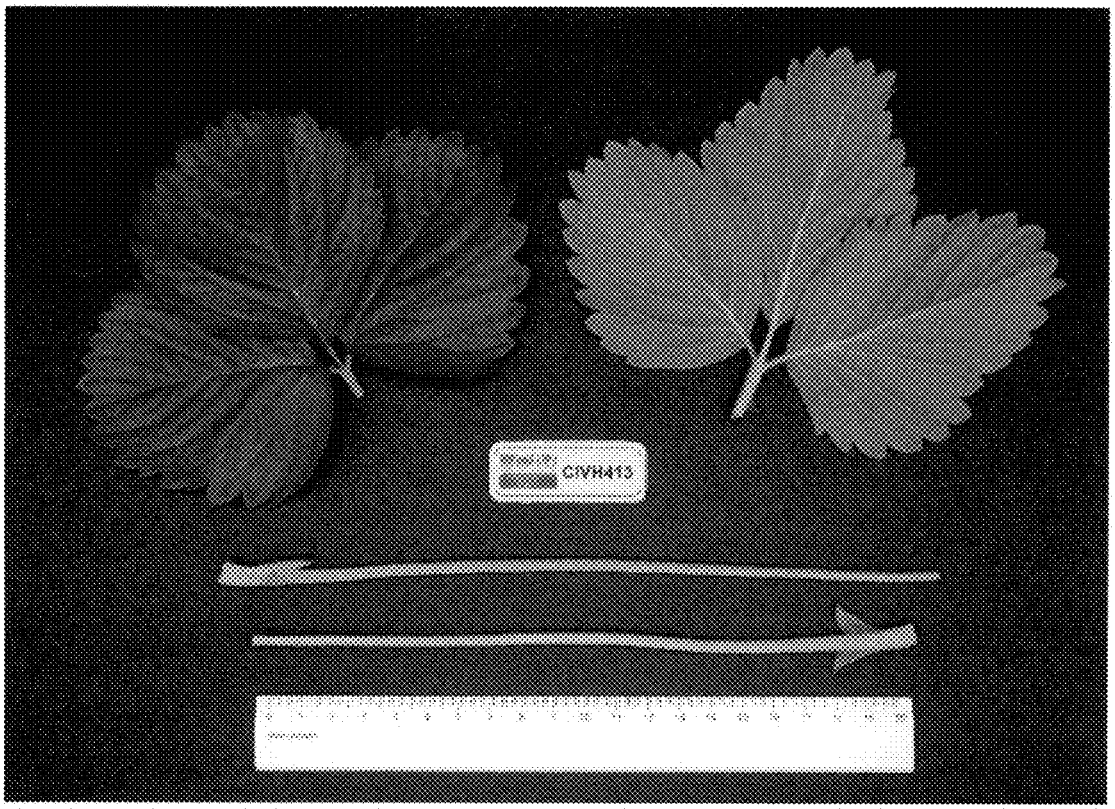
Figure 3:
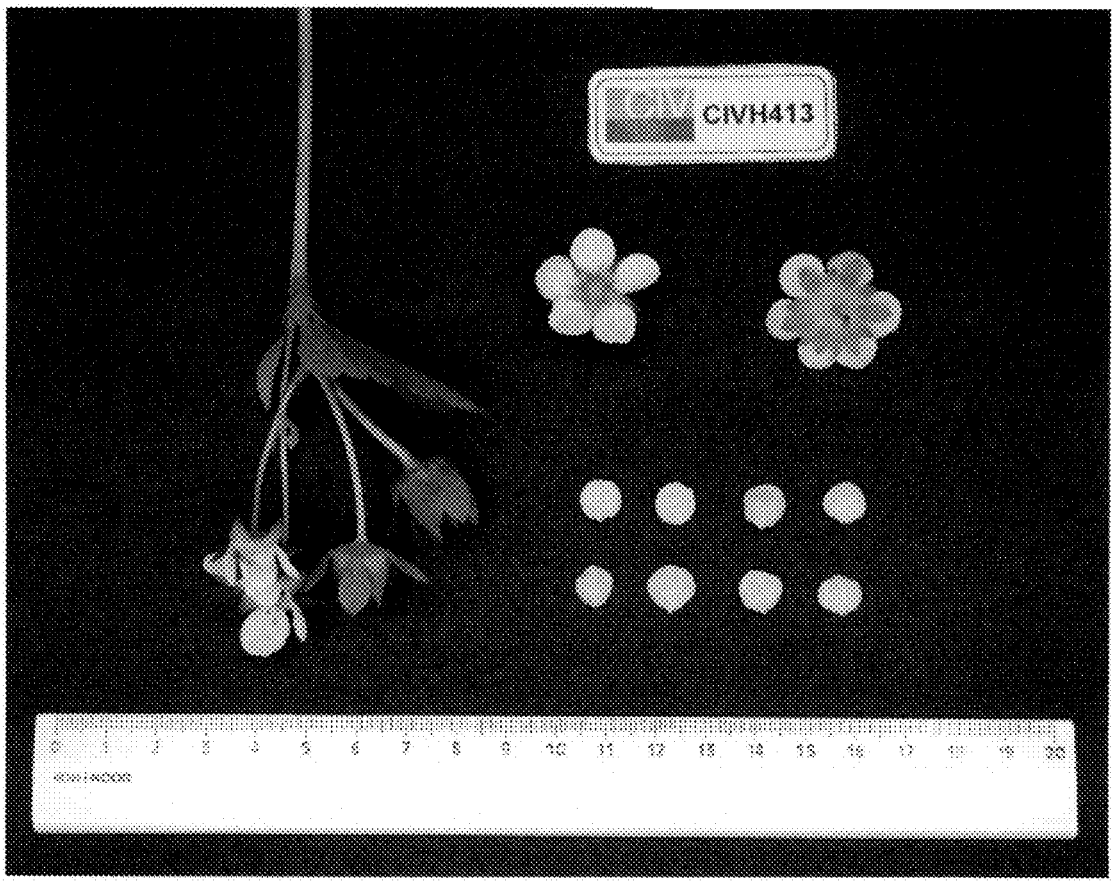
Figure 4:
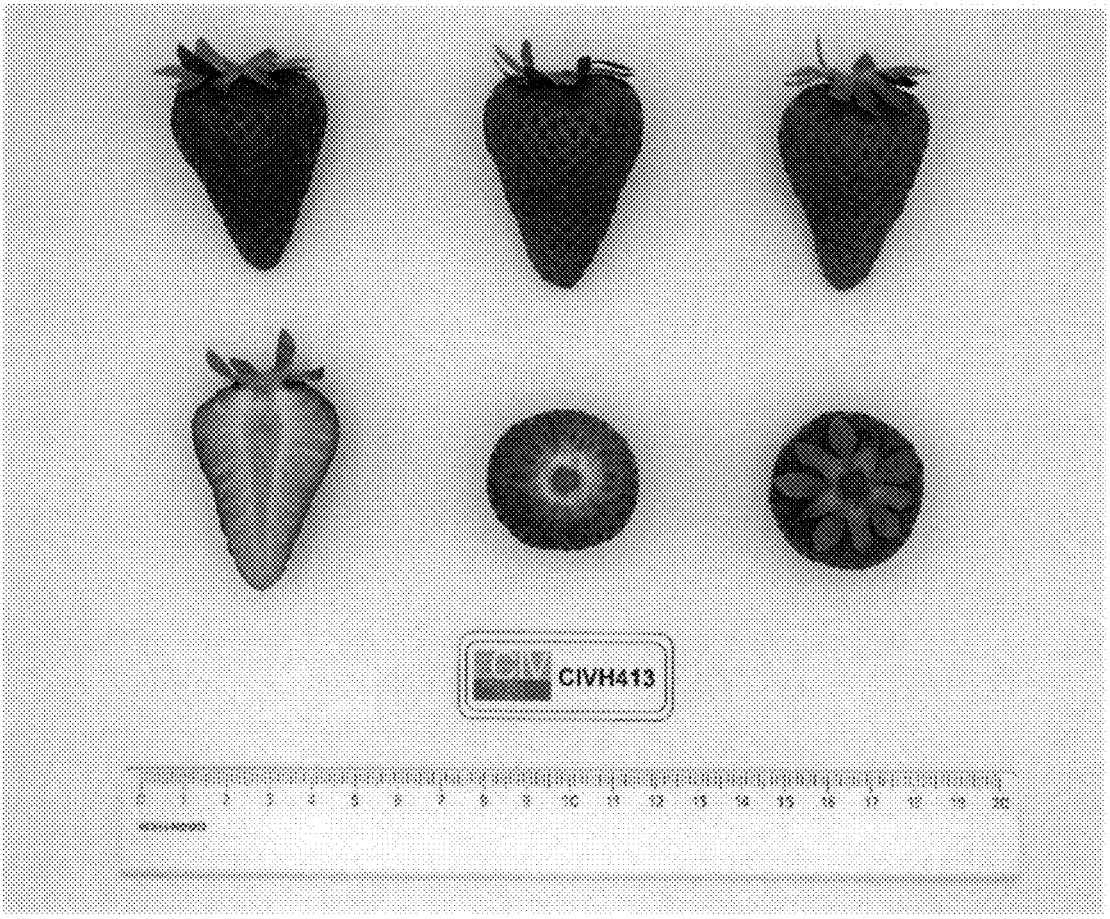

FIG. 1 shows plants of 'CIVH413';
FIG. 2 shows the leaves of 'CIVH413';
FIG. 3 shows typical flowers of 'CIVH413'; and
FIG. 4 shows typical fruits of 'CIVH413'.

DETAILED BOTANICAL DESCRIPTION

'CIVH413' has not been observed under all possible environmental conditions. The characteristics of the new variety may vary in detail, depending upon variations in environmental factors, including weather (temperature, humidity and light intensity), day length, soil type and location.

The aforementioned photographs, together with the following observations, measurements and values describe the new strawberry variety 'CIVH413', unless otherwise noted, taken during 2022 growing season in San Giuseppe di Comacchio, Ferrara, Italy. The observations, measurements and values were taken from plants of 'CIVH413' dug in December 2020 from a nursery located in 44021 Codigoro, Ferrara, (locality Pomposa), Italy, and planted in July 2021 in a test field in San Giuseppe di Comacchio, Ferrara, Italy.

From December 2020 to July 2021, the plants were stored in cold room, in order to undergo the hours of cold necessary for the correct development of the plants. Plants of the new strawberry variety 'CIVH413' were grown under conditions which closely approximate those generally used in commercial practice.

The observed plants were one year old plants. The plants used in the production field are produced in a nursery located in 44021 Codigoro, Ferrara, (locality Pomposa), Ferrara, Italy.

Yield observations and fruit quality characteristics are averaged from 3 years of data collected from the 2020 through 2022 growing seasons. Flower measurements and characteristics are from secondary flowers unless otherwise noted. Fruit characteristics and measurements are from secondary fruit unless otherwise noted.

Color references are made to The 1986 Royal Horticultural Society Colour Chart (R.H.S.), except where general colors of ordinary significance are used. Color values were taken under daylight conditions approximately in the afternoon in San Giuseppe di Comacchio, Ferrara, Italy. The age of the observed plants is one year old.

The following tables 3-9 describe fruit, plant, stolon, foliage, fruiting truss, flower and pest/disease characteristics of the new strawberry 'CIVH413'.

TABLE 3

FRUIT CHARACTERISTICS

| Characteristic | 'CIVH413' |
|---|---|
| Color of mature fruit | Red group - RHS 44B |
| Color of internal flesh | Red group - RHS 41B |
| Color of internal core | Red group - RHS 41B |
| Length (cm) | About 5.0 cm |
| Width (cm) | About 3.5 cm |
| Ratio length/width | Moderately longer |
| Calyx diameter (cm) | About 3.4 cm |
| Average weight (gm) | About 26.10 g |
| Achene color | Yellow-green group 150C |
| Number of achenes per $cm^2$ measured at the center of berry | About 7 |
| Average weight of 1000 achenes (g) | About 0.80 g |
| Marketable yield (gm/plt) | Average 1050 gm/plt |
| Size | Large |
| Predominant shape | Conical |
| Difference in shapes between primary and secondary fruit | Slight |
| Band without achenes | Narrow |
| Unevenness of surface | Even or slightly uneven |
| Evenness of color | Strong |
| Glossiness | Strong |
| Insertion of achenes | Level with surface |
| Insertion of calyx | Level with fruit |
| Attitude of the calyx | Outward |
| Size of calyx in relation to fruit diameter | Smaller |
| Adherence of calyx | Strong |
| Firmness of skin | Very firm |

TABLE 3-continued

| FRUIT CHARACTERISTICS | |
|---|---|
| Characteristic | 'CIVH413' |
| Firmness of flesh | Very firm |
| Distribution of red color of the flesh | Uniform |
| Hollow center expression | Absent or small |
| Flavor | Very good flavour, balanced and aromatic |
| Soluble solids (% brix) | About 7.4% |
| Time of first flowering | Early. The full bloom of first flowering is at the end of march, in North Italy - Po Valley |
| Time of first harvesting | Early. The first harvest period is from the beginning of May to the end of May, in North Italy - Po Valley |
| Harvest period | From the middle of May to the beginning of June in San Giuseppe di Comacchio, Ferrara, Italy |
| Type of bearing | Not remontant |

TABLE 4

| PLANT CHARACTERISTICS | |
|---|---|
| Characteristic | 'CIVH413' |
| Height (cm) | About 20 to 25 cm |
| Spread (cm) | About 30 to 40 cm |
| Size | Medium |
| Habit | Upright |
| Density | Medium |
| Vigor | Medium |

TABLE 5

| STOLON CHARACTERISTICS | |
|---|---|
| Characteristic | 'CIVH413' |
| Average number per plant | About 10-15 |
| Typical and Average length | 40 (cm) |
| Anthocyanin coloration | Red group - 53B |
| Anthocyanin intensity | Medium |
| Diameter at bract (mm) | About 3 mm |
| Pubescence | Sparse to medium |

TABLE 6

| FOLIAGE CHARACTERISTICS | |
|---|---|
| Characteristic | 'CIVH413' |
| Foliage: | |
| Color of upper surface | Green group - 137A |
| Color of underside | Green group - 138B |
| Shape in cross section | Concave |
| Interveinal blistering | Medium |
| Glossiness | Medium |
| Number of leaflets | 3 |
| Entire leaf size: | |
| Length: | About 12.5 cm |
| Width | About 16 cm |

TABLE 6-continued

| FOLIAGE CHARACTERISTICS | |
|---|---|
| Characteristic | 'CIVH413' |
| Terminal Leaflet: | |
| Length (cm) | About 9.0 cm |
| Width (cm) | About 8.1 cm |
| Length/width ratio | Equal |
| Serrations/leaf | Overlapping |
| Size | Medium |
| Shape of base | Obtuse |
| Shape of teeth | Acute to rounded |
| Petiole: | |
| Color of petiole | Yellow-Green group - 144B |
| Length (cm) | About 24.5 cm |
| Diameter (mm) | About 0.4 cm |
| Pubescence | Medium |
| Attitude of hairs | Slightly outwards |
| Stipule: | |
| Shape of stipule | narrow-elliptic |
| Length (mm) | About 2.85 cm |
| Width (mm) | About 9 mm |
| Anthocyanin coloration | Absent or very weak (Greyed-Purple-186B) |
| Color | Yellow-green group 145C |

TABLE 7

| FRUITING TRUSS CHARACTERISTICS | |
|---|---|
| Characteristic | 'CIVH413' |
| Length (cm) | About 20-25 cm |
| Attitude | Erect |
| Position relative to foliage | Same level |
| Number of fruit per truss | 1 to 5 |
| Pubescence | Strong |
| Anthocyanin intensity | Absent or very weak (Greyed-Purple-186B) |
| Attitude at first pick | Horizontal |

TABLE 8

| FLOWER CHARACTERISTICS | |
|---|---|
| Characteristic | 'CIVH413' |
| Petal color | |
| Mature (upper) | White group - 155D |
| Mature (lower) | White group - 155D |
| Petal shape | |
| Overall | Circular |
| Apex | Rounded |
| Base | Rounded |
| Petal length (mm) | About 1 to 1.2 cm |
| Petal width (mm) | About 1 to 1.2 cm |
| Petal length/width ratio | Equal |
| Number of petals/flower | About 5 to 6 |
| Sepals color | |
| Mature (upper) | Green group - 137A |
| Mature (lower) | Green group - 138A |
| Sepal shape | |
| Overall | Elliptic |
| Apex | Pointed |
| Base | Flat |
| Sepal length (mm) | About 0.7 to 1.2 cm |
| Sepal width (mm) | About 0.3 to 0.5 cm |

TABLE 8-continued

| FLOWER CHARACTERISTICS | |
|---|---|
| Characteristic | 'CIVH413' |
| Sepal length/width ratio | Longer |
| Number of sepals/flower | About 9 to 13 |
| Corolla diameter (mm) | About 21 mm |
| Calyx diameter (mm) | About 28 mm |
| Size of calyx relative to corolla | Larger |
| Size of inner calyx relative to outer calyx | Smaller |
| Relative position of petals | Touching |

TABLE 9

| REPRODUCTIVE ORGANS | |
|---|---|
| Characteristic | 'CIVH413' |
| Receptacle color | Yellow green group - 154B |
| Pollen color | Yellow orange group - 14A |
| Stamen | Present |
| Stamen: | Numerous |
| Length: | Approximately 2.7 mm. Color: RHS 144 D yellow-green group |
| Anthers: | Generally average in size (length: about 1.0 mm, width: about 0.75 mm). Color: RHS 15 B yellow orange group and darkening with advanced maturity. |

TABLE 9-continued

| REPRODUCTIVE ORGANS | |
|---|---|
| Characteristic | 'CIVH413' |
| Pistils: | Numerous, generally average in size. Color: 151 D green group. |
| Pollen amount: | Much |
| Fruit use: | Fresh consumption |
| Shipping quality: | High |

TABLE 10

| PEST AND DISEASE REACTIONS | |
|---|---|
| Characteristic | 'CIVH413' |
| Powdery mildew (*Sphaerotheca macularis*) | Moderately tollerant |
| Angular leaf spot (*Xanthomonas fragariae*) | Moderately susceptible |
| Botrytis fruit rot (*Botrytis cinerea*) | Very low sensibility |
| Fusarium wilt (*Fusarium oxysporum*) | Moderately susceptible |
| Anthracnose crown rot (*Colletotrichum fragariae*) | Moderately susceptible |
| Two-spotted spider mite (*Tetranychus urticae*) | Susceptible |

I claim:

1. A new and distinct strawberry plant named 'CIVH413', as herein described and illustrated.

* * * * *